US010973622B2

(12) United States Patent
Mackay

(10) Patent No.: US 10,973,622 B2
(45) Date of Patent: Apr. 13, 2021

(54) INTERNAL BRACE FOR TISSUE REPAIRS AND REINFORCEMENTS

(75) Inventor: Gordon M. Mackay, Perthshire (GB)

(73) Assignee: ARTHREX, INC., Naples, FL (US)

(*) Notice: Subject to any disclaimer, the term of this patent is extended or adjusted under 35 U.S.C. 154(b) by 371 days.

(21) Appl. No.: 13/455,581

(22) Filed: Apr. 25, 2012

(65) Prior Publication Data
US 2012/0271416 A1 Oct. 25, 2012

Related U.S. Application Data

(60) Provisional application No. 61/478,720, filed on Apr. 25, 2011.

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61B 2017/044* (2013.01);
(Continued)

(58) Field of Classification Search
CPC ........ A61F 2/08; A61F 2/0811; A61F 2/0805; A61F 2002/0817; A61F 2002/0823; A61F 2002/0829; A61F 2002/0835; A61F 2002/0841; A61F 2002/0847; A61F 2002/0852; A61F 2002/0858; A61F 2002/0864; A61F 2002/087; A61F 2002/0876; A61F 2002/0882;
(Continued)

(56) References Cited

U.S. PATENT DOCUMENTS 5,281,422 A * 1/1994 Badylak et al. ........... 623/13.11
7,329,272 B2    2/2008 Burkhart et al.
(Continued)

FOREIGN PATENT DOCUMENTS

WO    2008/060361 A2    5/2008
WO    WO 2009113076 A1 * 9/2009 ............... A61F 2/08
WO    WO 2010030714 A2 * 3/2010 ............. A61L 27/24

OTHER PUBLICATIONS

Rue et al., Minimally invasive Medial Collateral Ligament Reconstruction Using Achilles Tendon Allograft. Techniques in Knee Surgery. 2007, 6(4):266-273.*
(Continued)

*Primary Examiner* — Jerrah Edwards
*Assistant Examiner* — Rokhaya Diop
(74) *Attorney, Agent, or Firm* — Carlson, Gaskey & Olds

(57) ABSTRACT

A reconstruction system and associated techniques for soft tissue repairs and repair augmentation. The reconstruction system is an internal soft tissue brace formed of at least one fixation device (for example, anchors or screws) and a replacement/reinforcement construct (for example, a suture construct in the form of a suture tape such as FiberTape® or a collagen tape or a suture with biological material or a collagen coated material, or a collagen patch, or a biological construct such as Arthroflex). The reinforcement construct and fixation devices may be used as a suture repair alone (to replace the ligament or tendon), or in conjunction with other traditional soft tissue repair procedures, acting as a reinforcement system for the repaired soft tissue.

1 Claim, 10 Drawing Sheets

(52) U.S. Cl.
CPC ............... *A61F 2002/0858* (2013.01); *A61F 2002/0888* (2013.01)

(58) Field of Classification Search
CPC ......... A61F 2002/0888; A61B 17/0401; A61B 2017/044
USPC ......... 623/13.11, 13.12, 13.13, 13.14, 13.15, 623/13.16, 13.17, 13.18, 13.19, 13.2; 606/232
See application file for complete search history.

(56) References Cited

U.S. PATENT DOCUMENTS

| | | | |
|---|---|---|---|
| 8,226,715 | B2 | 7/2012 | Hwang et al. |
| 9,579,129 | B2 | 2/2017 | Bonutti |
| 9,999,449 | B2 | 6/2018 | Bonutti |
| 2009/0187216 | A1* | 7/2009 | Schmieding ....... A61B 17/0401 606/232 |
| 2009/0198288 | A1* | 8/2009 | Hoof et al. ................... 606/301 |
| 2009/0222039 | A1* | 9/2009 | Dreyfuss et al. ............. 606/229 |

OTHER PUBLICATIONS

Legnani et al., Anterior Cruciate Ligament Reconstruction with Synthetic Grafts: a review of literature. International Orthopaedics. 2010, 34(465):465-471.*

Machotka et al., Anterior Cruciate Ligament Repair with LARS (Ligament Advanced Reinforcement System): a systematic review. Sports Medicine, Arthroscopy, Rehabilitation, Therapy & Technology. 2010, 2(29): 1-10.*

Corin. ACL Reconstruction with LARS Ligament Surgical Technique (Brochure) 2009.*

Kdolsky et al. Braided Polypropylene Augmentation Device in Reconstructive Surgery of the Anterior Cruciate Ligament: Long-Term Clinical Performance of 594 Patients and Short-Term Arthroscopic Results, Failure Analysis by Scanning Electron Microscopy, and Synovial Histomorphology. Journal of Orthopaedic Research, 1997. vol. 15 (1): 1-10.*

Fridman et al. "Augmented Brostrom Repair Using Biologic Collagen Implant: Report on 9 Consecutive Patients." The Foot & Ankle Journal. (Year: 2008).*

Hentges et al. Chronic Ankle and Subtalar Joint Instability in the Athlete. Clinics in Podiatric Medicine and Surgery, 28(1), pp. 87-104, Jan. 2011. (Year: 2011).*

Lind et al., Anatomical Reconstruction of the Medial Collateral Ligament and Posteromedial Corner of the Knee in Patients With Chronic Medial Collateral Ligament Instability. The American Journal of Sports Medicine, 37(6), 2009 pp. 1116-1122. (Year: 2009).*

Ellis et al., Results of Anatomic Lateral Ankle Ligament Reconstruction with Tendon Allograft. HSS Journal, [online] 7(2), pp. 134-140, Mar. 2011.

Fridman, et al., Augmented Brostrom Repair Using Biologic Collagen Implant Report on 9 Consecutive Patients; The Foot & Ankle Journal, vol. 1, No. 7, Jul. 2008.

Groth, et al., Lateral Ankle Ligament Injuries in Athletes: Diagnosis and Treatment; Operative Techniques in Sports. Medicine, 18:18-26, 2010 Elsevier Inc.

* cited by examiner

INTERNAL BRACE FOR TISSUE REPAIRS AND REINFORCEMENTS

CROSS-REFERENCE TO RELATED APPLICATIONS

This application claims the benefit of U.S. Provisional Application No. 61/478,720 filed Apr. 25, 2011, the entire disclosure of which is incorporated by reference herein.

FIELD OF THE INVENTION

The present invention relates to the field of surgery and, in particular, to devices and techniques for replacement, reattachment and/or reinforcement of soft tissue such as tendon or ligament.

BACKGROUND OF THE INVENTION

Ligaments and tendons are soft collagenous tissues that play a significant role in musculoskeletal biomechanics. Ligaments connect bone to bone and tendons connect muscles to bone.

Repairing torn ligaments poses significant challenges for physicians. Some of the repairs include grafting tissue or placing artificial prostheses to replace ligaments. Often patients have to undergo multiple surgeries to maintain a repair, or have to have prostheses replaced.

Some of the torn ligaments most difficult to repair are those around the knee. The four major stabilizing ligaments of the knee are the anterior and posterior cruciate ligaments (ACL and PCL, respectively), and the medial and lateral collateral ligaments (MCL and LCL, respectively). The MCL, for example, is critical to the stability of the knee joint (spanning the distance from the end of the femur to the top of the tibia) and is located on the inside of the knee joint. The MCL resists widening of the inside of the joint, or prevents "opening-up" of the knee.

Because the MCL resists widening of the inside of the knee joint, the ligament is usually injured when the outside of the knee joint is struck. This force causes the outside of the knee to buckle, and the inside to widen. When the MCL is stretched too far, it is susceptible to tearing and injury.

Treatment of an MCL tear depends on the severity of the injury but often includes surgery with bracing and/or casting and immobilization. Bracing may cause complications such as stiffness or adhesions from limiting normal knee range of motion. The torn segments of the MCL are reattached (sewn together) to the original configuration but the reattachment is susceptible to additional tears and breaks and the ligament is also prone to losing its normal stretch and elasticity. Generally, primary direct surgical repair of the MCL has a poor outcome. A combined ACL and MCL injury often requires ACL reconstruction and a brace for the MCL, which compromises rehabilitation (i.e., prolongs rehabilitation associated with bracing). In addition, excessively loading of the ACL due to MCL attenuation is a recognized cause of graft failure and subsequent revision. The MCL laxity also predisposes to ACL rupture and the recurrent instability accelerates the arthritic process.

Medial patello-femoral ligament (MPFL) reconstruction is a procedure used to correct serious and recurring dislocation of the kneecap. MPFL reconstruction typically involves reattachment of the torn segments or using a ligament taken from elsewhere in the body or a synthetic replacement, to keep the kneecap in the trochlear groove, preventing dislocation.

The ligaments of the ankle joint (i.e., the lateral collateral ligaments and the medial collateral ligaments) are strong fibrous bands; however, they are often susceptible to injury due to the excessive movement of the subtalar joint during activity. In the United States alone, about 28,000 acute lateral ankle sprains are treated every day. Like in the knee or patellar repairs, the ankle ligament repairs often require reattachment of the torn segments and use of a brace and/or casting and extensive rehabilitation. Current management of ankle instability involves (i) immobilization (despite universally considered to be detrimental to joint function); (ii) stiffness, wasting, and prolonged rehabilitation which do not address associated intra-articular pathology; and (iii) recurrent instability that accelerates the arthritic process.

Successful and less invasive acute repairs that reduce progression to chronic instabilities and reconstruction procedures are needed. Also needed are devices and less invasive repairs for tissue reconstruction that improve primary repair outcomes without the cost of bracing, casting and/or delayed rehabilitation.

SUMMARY OF THE INVENTION

The present invention provides techniques and devices for replacement and reattachment of soft tissue (such as ligaments or tendons) and/or reinforcement of such reattached soft tissue.

The present invention provides an "internal soft tissue brace" and associated techniques according to which acute injury of soft tissue (for example, ligament or tendon) is treated with fixation devices (for example, anchors or screws) and a replacement/reinforcement construct (for example, a suture construct in the form of FiberTape®) or collagen tape, a collagen patch, or a biological construct such as Arthroflex®).

The replacement/reinforcement construct and fixation devices may be used in lieu of natural anatomical soft tissue (ligament or tendon) to replace the soft tissue, or may be used in conjunction with other traditional soft tissue repair procedures (for example, in conjunction with a repaired/reattached ligament, or with a replacement ligament taken from elsewhere in the body, or with a synthetic replacement) acting as a reinforcement for the repaired/reattached soft tissue.

The invention also provides an "internal soft tissue brace" kit comprising inter alia fixation devices (for example, screws or anchors such as SwiveLocks®(Arthrex)) and at least one replacement/reinforcement construct (for example, a suture construct such as a collagen strand or a FiberTape®, or a collagen patch, or a biological construct such as Arthroflex®) with disposable passing instruments and accessories, to simplify the overall surgical procedure and augment the ligament/tendon repair, while reinforcing the reconnected ligament/tendon.

An exemplary method of soft tissue reconstruction of the present invention comprises inter alia the steps of: (i) attaching torn segments of soft tissue (such as tendon or ligament); (ii) reinforcing the attached segments of soft tissue by providing a reinforcement construct (such as FiberTape® or collagen tape, among others) and fixation devices such as screws or anchors, for example; and optionally (iii) delivering a biological material (such as blood, bone marrow aspirate (BMA), bone marrow stem cells (BMSCs), platelet rich plasma (PRP), autologous conditioned plasma (ACP), and/or growth factors) to the soft tissue site to promote soft tissue healing.

DETAILED DESCRIPTION OF THE INVENTION

Figure 2:
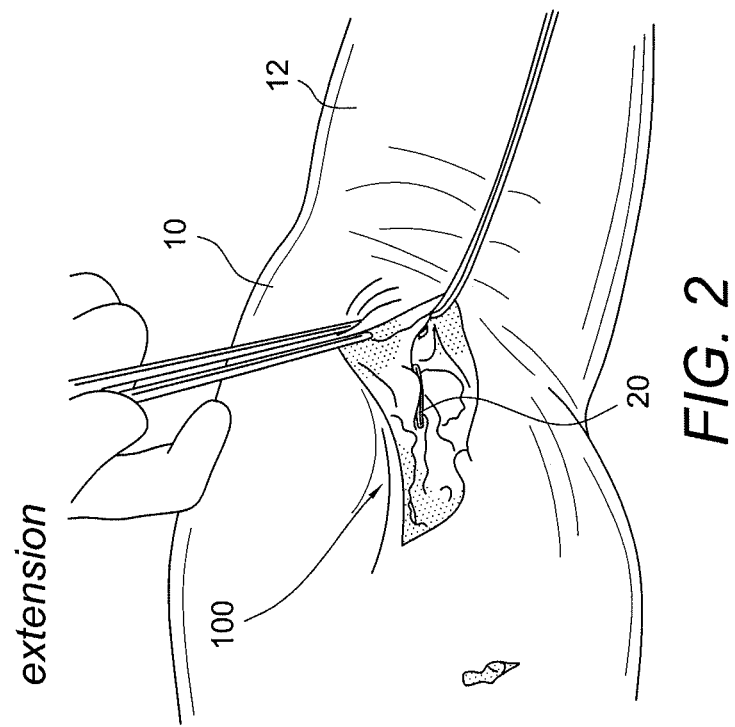
FIG. 2 illustrates an MCL internal brace used in a method of MCL reconstruction of the present invention (with the internal brace after insertion and with the knee in extension).

The present invention provides an "internal soft tissue brace" (reconstruction system, internal brace, or Internal-Brace™) and associated techniques according to which acute injury of soft tissue (for example, MCL, LCL, MPFL, lateral ankle ligament and/or acromioclavicular joint ligaments, among others) is treated with percutaneous, stab incision placement of fixation devices (such as anchors, screws or staples, for example) adjacent to the origin and insertion of a disrupted ligament. A replacement/reinforcement construct (for example, a suture construct in the form of a suture tape such as FiberTape® or a FiberTape® coated with collagen or a collagen tape or a suture with biological material or a collagen coated material, a collagen patch, or a biological construct such as Arthroflex®, among others) is passed under the skin, muscle and fascia between the fixation devices (for example, two anchors or screws) to replace and/or reinforce the repaired or attenuated ligament.

The distal fixation point is approximated with another fixation device (for example, another anchor or screw) and the replacement/reinforcement construct (for example, FiberTape®) and joint range of motion isometry is tested and confirmed. A drill hole at the metal tipped mark of the anchor allows anatomic fixation of the distal anchor and reinforcement construct, as a minimally invasive augmentation of the injured ligament.

The replacement/reinforcement construct and fixation devices act as an "internal brace" that eliminates the need of a post operative brace or cast in post-injury treatment, allowing immediate motion and rehabilitation, accelerating wound healing, reattaching soft tissue and/or reinforcing the reattached soft tissue, resulting in an early return to daily living and sports. The fixation strength of the replacement/reinforcement construct (for example, FiberTape®) and the fixation devices (for example, anchors such as SwiveLock® C anchors or PushLock® C anchors, or screws such as interference screws or tenodesis screws, or combination of screws and anchors) is around 800N, which exceeds the strength of native ligaments.

The reconstruction system of the present invention comprises fixation devices/implants in the form of anchors and/or screws for example, SwiveLock® C anchors, or PushLock® C anchors, or tenodesis screws or interference screws, or combinations of screws and anchors and of additional fixation devices. In exemplary embodiments only, and as detailed below, the fixation devices may be two small 3.5 mm or 4.75 mm anchors, or two SwiveLock® C anchors, or two PushLock® C anchors, or any combination of anchors and/or screws, which may be employed in conjunction with a suture construct (for example, a suture tape such as FiberTape® or a collagen tape) attached to the fixation devices. The fixation devices/implants may have various sizes, i.e., various diameters and/or lengths depending on the characteristic of the soft tissue and/or bones and muscles where soft tissue is replaced, attached or reconnected. The fixation devices may be formed of biocompatible materials such as polyetheretherketone (PEEK), poly L lactic acid (PLLA), biocomposite materials, or any biocompatible material including metals and metal alloys, or combination of such materials, for example.

According to an exemplary embodiment only, the fixation devices of the reconstruction system are placed adjacent the reattached ligament/tendon (i.e., adjacent the torn segments or parts of ligament/tendon that are reconnected and reattached) and adjacent to the origin and insertion of a Grade II and higher disrupted ligament. The suture construct is passed under the skin, muscle and fascia between the fixation devices (for example, two anchors or screws) to reinforce the repaired or reattached ligament/tendon.

A biological material such as blood, blood components, BMA, BMSCs, PRP, ACP and/or growth factors may be provided at (for example, injected into) the ligament injury site and small incisions and/or into the reinforcement construct, to further improve and accelerate incision and ligament healing.

The invention also provides an "internal soft tissue brace" kit (a ligament repair augmentation kit) comprising inter alia fixation devices (for example, a plurality of screws, staples or anchors such as SwiveLock®or PushLock®anchors) and at least one replacement/reinforcement construct (for example, a suture construct in the form of a suture tape such as FiberTape® or a collagen tape or a suture with biological material, or a collagen patch, or a biological construct such as Arthroflex®, among others) with passing instruments and accessories, to simplify the overall surgical procedure and augment the ligament/tendon repair, while reinforcing the reconnected ligament/tendon. The passing instruments and accessories may be disposable.

Referring now to the drawings, where like elements are designated by like reference numerals, FIGS. 1-13 illustrate exemplary embodiments of an internal soft tissue brace (reconstruction system or InternalBrace™ system) 100, 200, 300 of the present invention. The figures and embodiments below will be detailed and explained with reference to a replacement/reinforcement construct in the specific form of a suture construct; however, the invention is not limited to this specific embodiment and incorporates other resorbable and/or biological options that are not limited to sutures or suture tapes, such as Arthroflex® or various patches with biological materials, or strips of a cut patch, among many others.

The embodiments below will be also detailed and explained with reference to surgical techniques for soft tissue repairs using a minimally invasive approach; however, the invention is not limited to this specific embodiment and incorporates surgical techniques and procedures which include open incisions in lieu of the minimally invasive repairs.

The reconstruction system 100, 200, 300 of the present invention may be used as a primary procedure (i.e., employed for the actual replacement of the torn/damaged soft tissue) or, alternatively, may be used in conjunction with other traditional ligament/tendon repairs. For example, a surgeon may employ some type of biologic material to repair the torn soft tissue with the reconstruction system 100, 200, 300 of the present invention. In this case, the reconstruction system 100, 200, 300 of the present invention (the internal brace) will act as a reinforcement instead of a primary procedure. For example, the internal brace (reconstruction system) may be used with the addition of a tendon graft or a synthetic graft (primary repair) to augment the standard ligament repair procedure and to act as a reinforcement, supporting the primary repair. The internal brace (reconstruction system) may be also used as a suture repair alone. The dimensions (for example, length and width) of the replacement/reinforcement construct vary depending upon the specific characteristics of the ligament/tendon to be replaced or reinforced, with the length of the construct being about equal to the length of the ligament/tendon to be replaced or reinforced (i.e., the distance between the anatomical origin and insertion points of the ligament/tendon).

FIGS. 1-3

Figure 1:
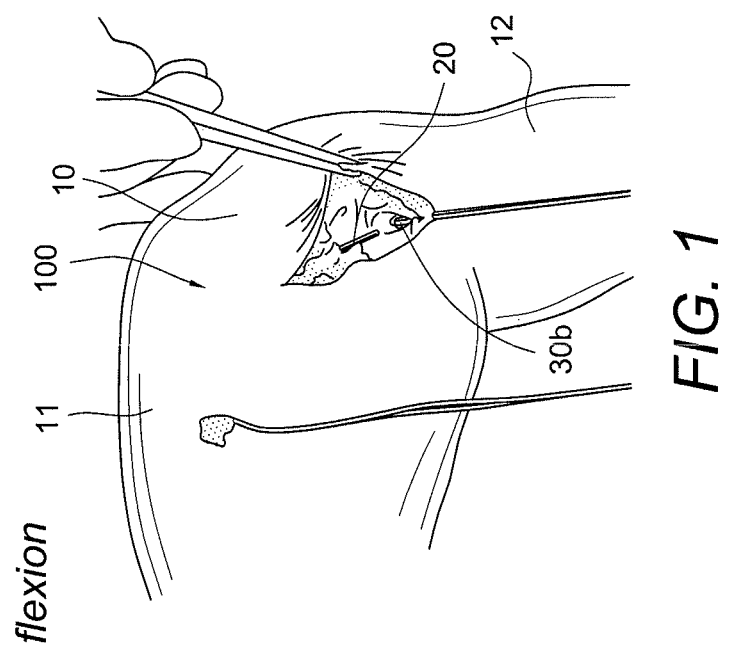
FIG. 1 illustrates an MCL internal brace used in a method of MCL reconstruction of the present invention (with the internal brace after insertion and with the knee in flexion).
Figure 3:
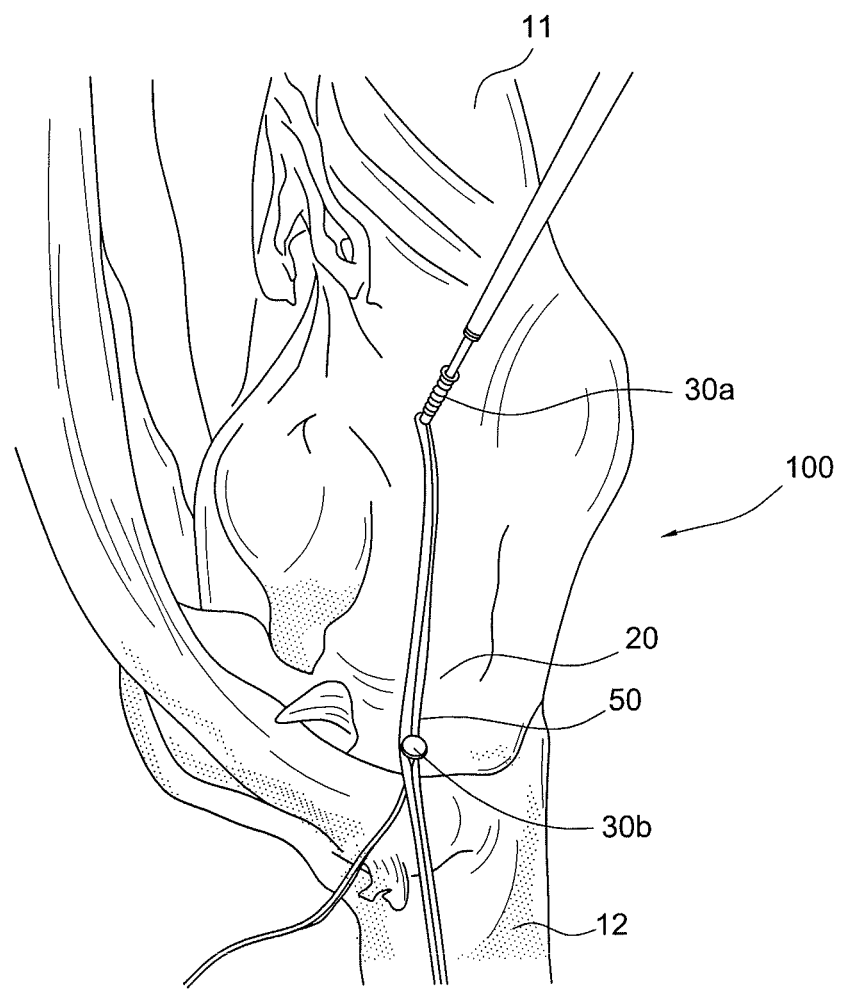
FIG. 3 illustrates another view of an MCL internal brace used in a method of MCL reconstruction of the present invention.

FIGS. 1-3 illustrate an MCL internal brace 100 (reconstruction system 100) used in a method of MCL reconstruction of the present invention. FIG. 1 shows the MCL internal brace 100 after insertion and with knee 10 in flexion, while FIG. 2 shows the MCL internal brace 100 after insertion and with the knee 10 in extension. MCL internal brace 100 comprises a replacement/reinforcement construct 20 (suture construct 20) attached to two fixation devices 30a, 30b (implants 30a, 30b). Suture construct 20 may be a suture tape such as FiberTape® disclosed in U.S. Patent Publication No. 2005/0192631, the disclosure of which is incorporated by reference in its entirety herein, or a combination of suture strand and suture tape. The suture construct 20 may be also a collagen tape, or a suture with biological material such as the one described in U.S. Publ. No. 2009/0222039, the disclosure of which is incorporated by reference in its entirety herein. The suture construct may be also formed by cutting a patch into strips and using the strips with the fixation devices.

A biological material such as blood, blood components, BMA, BMSCs, PRP, ACP and/or growth factors (or combinations of such materials) may be directly injected into the ligament injury site and small incisions, to further improve and accelerate incision and ligament healing, or may be provided via the suture construct (i.e., provided within the suture construct 20, for example).

The fixation devices 30a, 30b may include knotless fixation devices such as an Arthrex PushLock® C anchor, as disclosed and described in U.S. Pat. No. 7,329,272, the disclosure of which is hereby incorporated by reference in its entirety, or an Arthrex SwiveLock® C anchor as disclosed and described in U.S. Publ. No. 2007/0191849, the disclosure of which is hereby incorporated by reference in its entirety. The fixation devices 30a, 30b may be any anchors or screws (such as interference screws or tenodesis screws) or any combinations of anchors and screws. The fixation devices/implants 30a, 30b may have various sizes (various diameters and/or lengths) and may be formed of biocompatible materials such as PEEK, biocomposite materials, metals and/or metal alloys, or combination of such materials, among others.

Surgical steps for a method of MCL reconstruction with MCL internal brace 100 of the present invention are provided below:

The knee 10 is positioned in 90 degree flexion. Two fixation devices 30a, 30b (for example, two SwiveLock® screws 30a, 30b) are inserted about 2 mm above the anatomical origin and about 5 mm anterior to the center of the epicondyle of femur 11. Use of a screen with template is optional.

Drop a line to mid point of tibia 12 about parallel to MCL fibers 50 (in line with MCL ligament 50). Secure just proximal to the upper border pes anserinus after testing range of motion (ROM).

Make about 1 cm longitudinal incision. Tunnel the curved blunt tip of a suture passer proximally between the points. After a blunt dissection under the subcutaneous fat, retrieve the suture construct 20 (the double strand FiberTape® 20).

Secure the FiberTape® 20 distally with fixation device 30b (for example, a 5 mm SwiveLock® 30b) inserted about perpendicular to the cortex in 30 degrees of flexion after testing range of motion (ROM) and stability.

The replacement/reinforcement construct 20 (suture construct 20) located between the two inserted fixation devices 30a, 30b is about parallel to the anatomical position and orientation of the natural ligament/tendon (the MCL ligament 50), i.e., extends along the longitudinal axis of the MCL ligament 50. Preferably, the length of the replacement/reinforcement construct 20 is about equal to the length of the anatomical MCL ligament 50.

Indications for MCL Internal Brace 100
Grade 2/3 medial ligament injuries
Aim is to accelerate rehabilitation and prevent attenuation of MCL complex during healing
Surgical Benefits
Simple and safe
Minimally invasive
Time efficient (about 30 min procedure)
Does not complicate MCL reconstruction/advancement if subsequently required
Primary direct repair of MCL alone is not successful
Arthroscopic check at same time is optimal
PRP injections facilitate biological healing
Patient Benefits
Accelerated recovery
Optimal length for ligament healing
No need for cast/brace
Internal brace may protect from future injury Joint protection instability/arthritis PRP injections facilitate biological healing The method of MCL reconstruction with reconstruction system 100 detailed above offers a unique approach and a fundamental change to the management of acute ligament injury (e.g., medial ligament of knee and acute medial patellofemoral ligament). Together with biologics, the method acts as a primary intervention to improve outcomes. The procedure is minimally invasive and compliments all inside ACL reconstruction when indicated.

Figure 4:
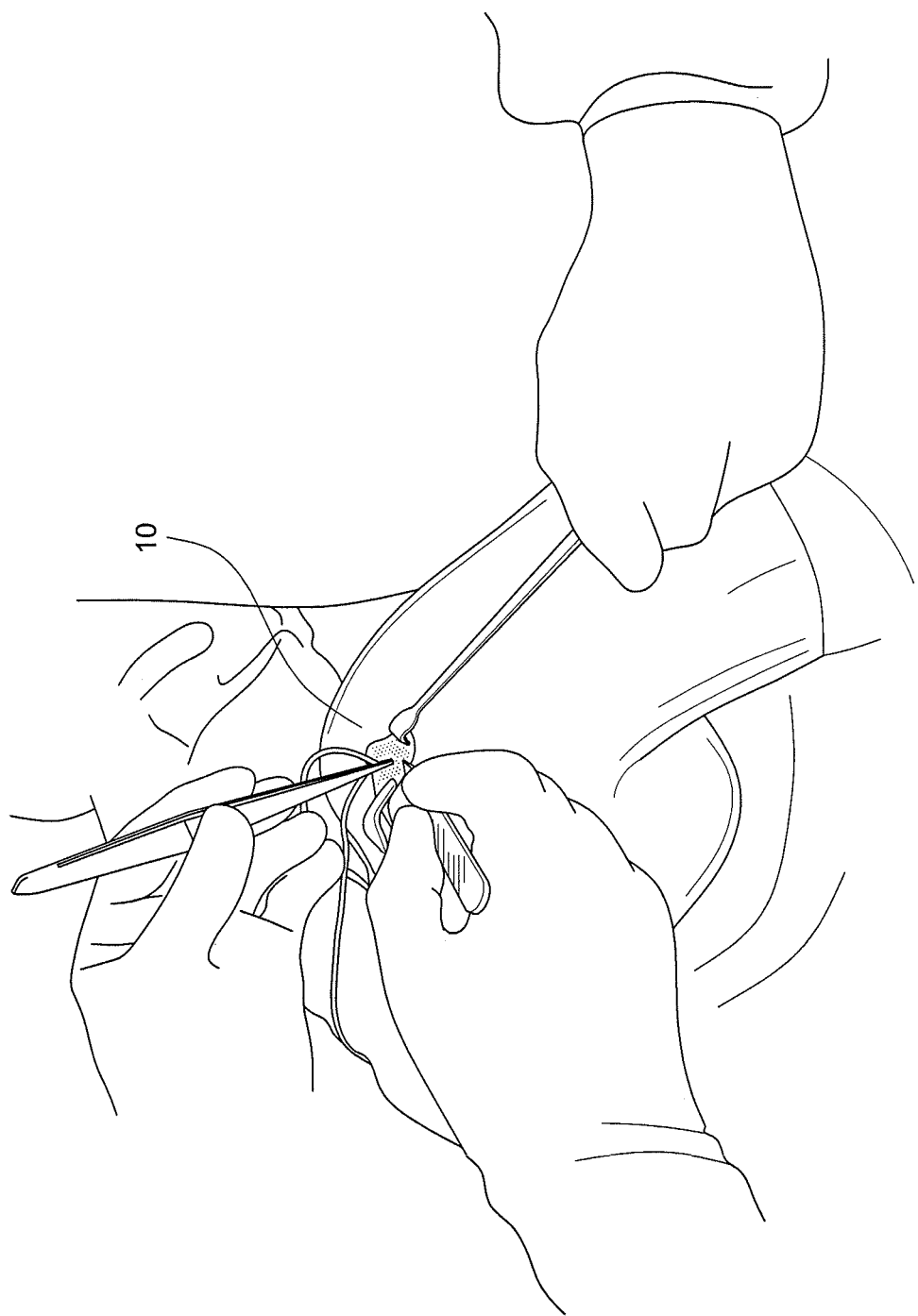
FIG. 4 illustrates a technique for patellofemoral (PF) joint using an internal brace of the present invention.
Figure 5:
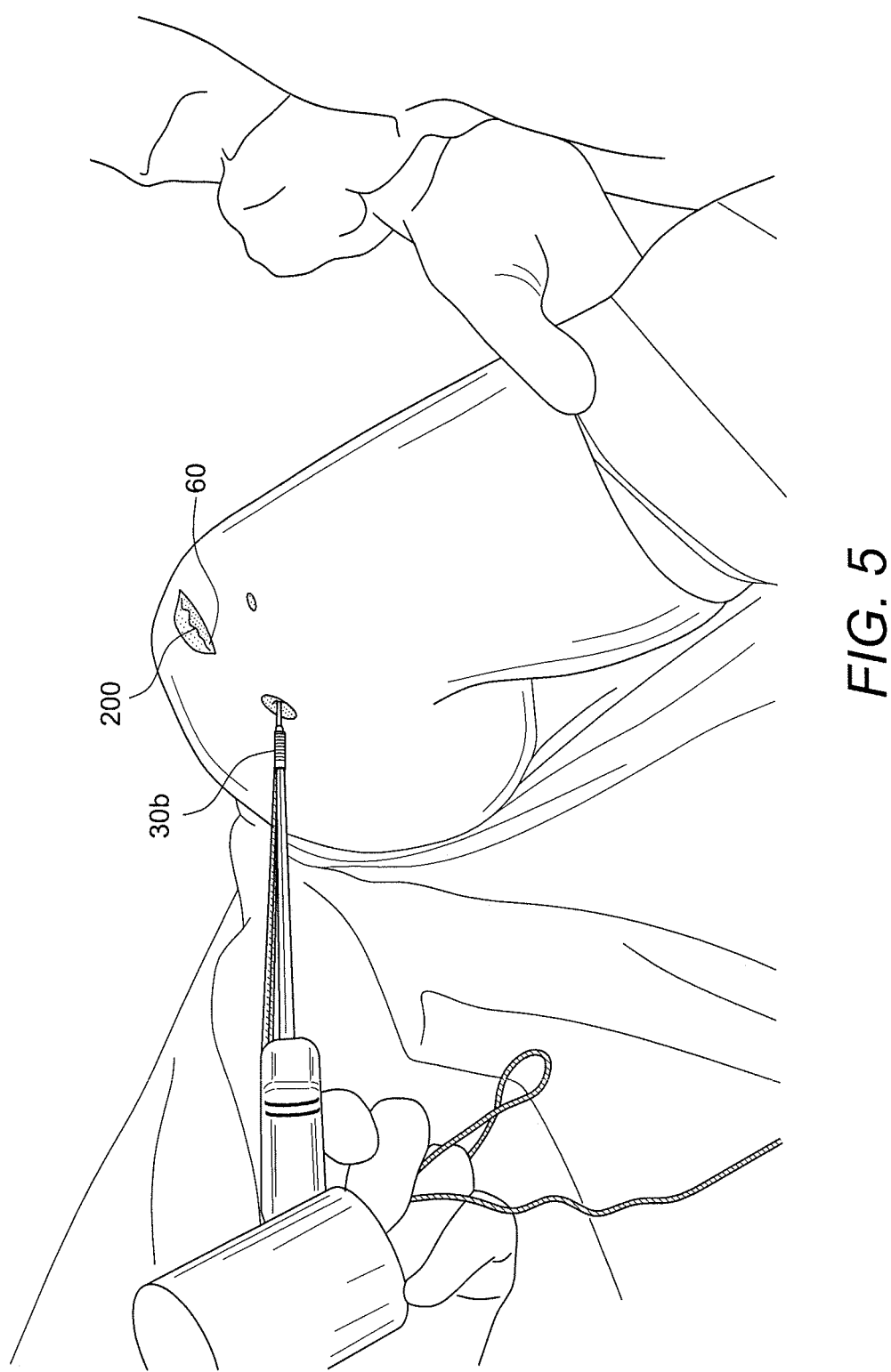
FIG. 5 illustrates the physiological tensioning through range to prevent over constriction.

FIGS. 4 and 5

FIGS. 4 and 5 illustrate a technique for patellofemoral (PF) joint repair/reinforcement using internal brace 200 of the present invention. FIG. 5 illustrates the physiological tensioning through range to prevent over constriction.

As in the above-described embodiment, the internal brace 200 may replace the PF ligament, for example, the medial patello-femoral ligament 60 (MPFL 60), or may be used in conjunction with a repaired/reattached MPFL 60 (as shown in FIG. 5), or in conjunction with a replacement ligament taken from elsewhere in the body or with a synthetic replacement. Internal brace 200 is similar to the internal brace 100 but differs only in that it is employed to replace and/or reinforce a different type of ligament (i.e., the PF ligament in lieu of the MCL) and, thus, the length of suture construct 20 varies depending upon the length of the anatomical ligament/tendon to be replaced/reinforced.

FIGS. 6-13

Figure 6:
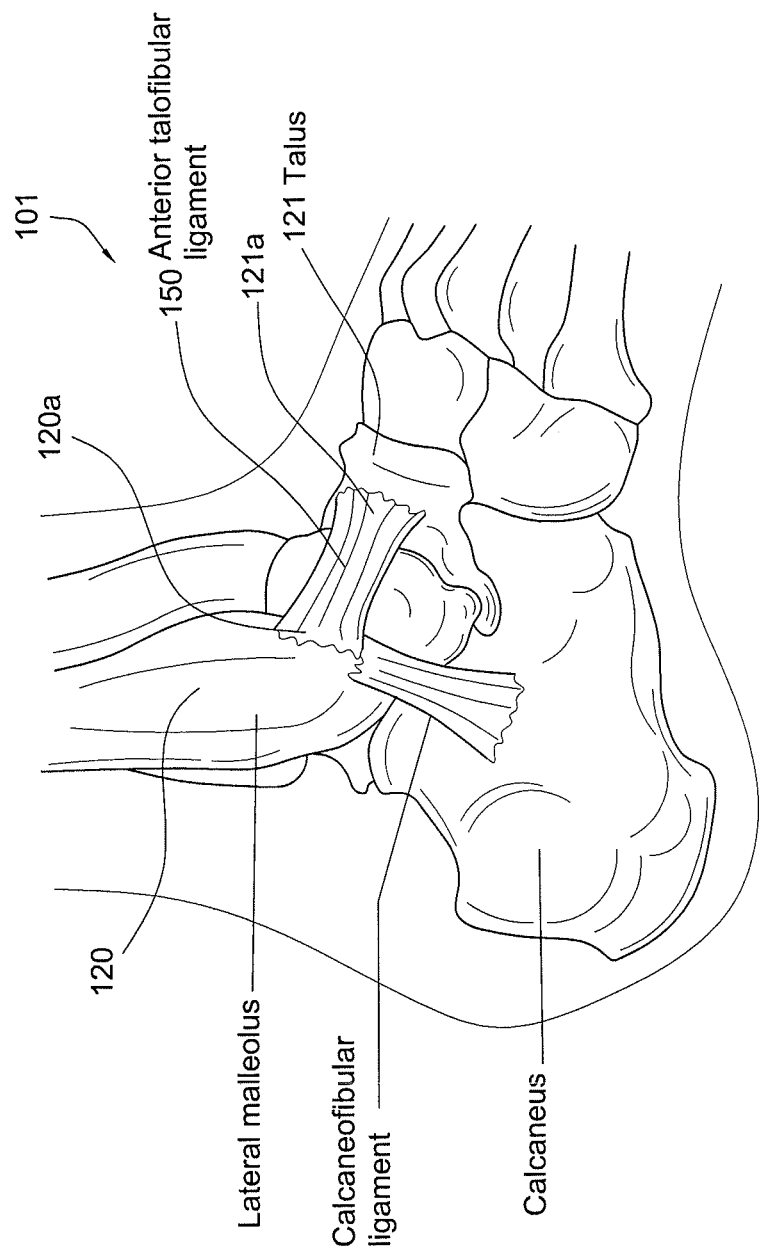
FIG. 6 illustrates a schematic view of a side of the ankle.

FIGS. 6-13 illustrate schematic views of a human ankle 101 and of an anterior talofibular ligament (ATFL) internal brace 300 used in a method of replacement/reconstruction/reinforcement of ATFL 150, according to the present invention. FIG. 6 illustrates a schematic view of a side of a human ankle 101 with anatomical ATFL 150 extending between a first location 120*a* (a first normal anatomical attachment or insertion point) in the fibular neck of fibula 120 and a second location 121*a* (a second normal anatomical attachment or insertion point) in talus 121.

Figure 8:
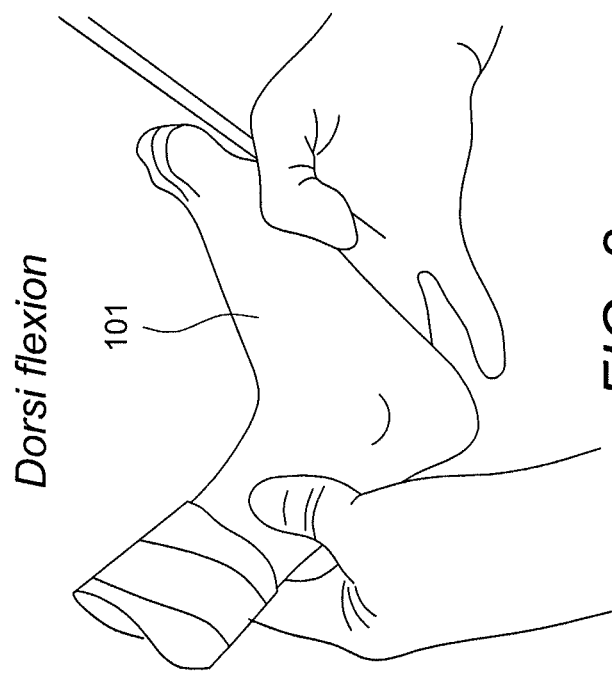
FIG. 8 illustrates the anatomical range after insertion of an ATFL internal brace used in a method of ATFL reconstruction of the present invention (with the ankle in dorsi flexion).
Figure 7:
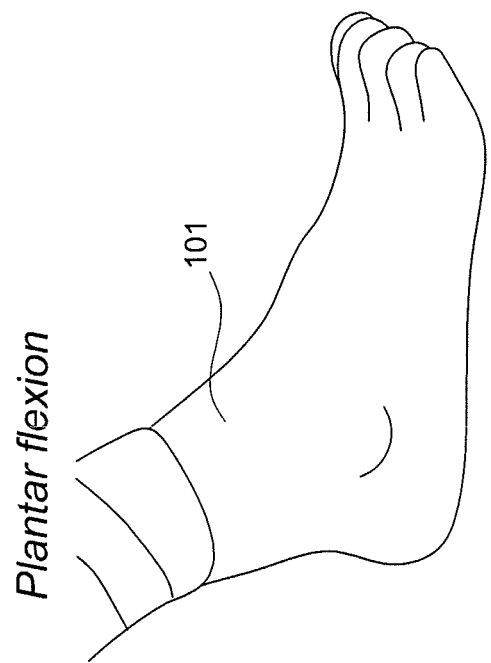
FIG. 7 illustrates the anatomical range after insertion of an anterior talofibular ligament (ATFL) internal brace used in a method of ATFL reconstruction of the present invention (with the ankle in plantar flexion).

FIG. 7 illustrates the anatomical range after insertion of the ATFL internal brace 300 used in a method of ATFL replacement/reinforcement of the present invention (with the ankle 101 in plantar flexion). FIG. 8 illustrates the anatomical range after insertion of the ATFL internal brace 300 (with the ankle 101 in dorsi flexion).

As in the above embodiments, the ATFL internal brace 300 replaces the anatomical ATFL 150 or, alternatively, reinforces the ATFL 150 (in case or tear or damage, in which case segments of torn or damaged ATFL 150 are reattached prior to or after attachment to the ATFL brace 300). The ATFL internal brace 300 may be also used with a ligament or tendon taken from somewhere else in the body or with a synthetic replacement that also acts as a reinforcement of the ATFL 150. Preferably, the ATFL internal brace 300 extends between a first location 120*a* (first normal anatomical attachment or insertion point) in the fibular neck of fibula 120 and a second location 121*a* (second normal anatomical attachment or insertion point) in talus 121, to parallel the anatomical orientation and position of the normal anatomic ATFL 150.

Figure 13:
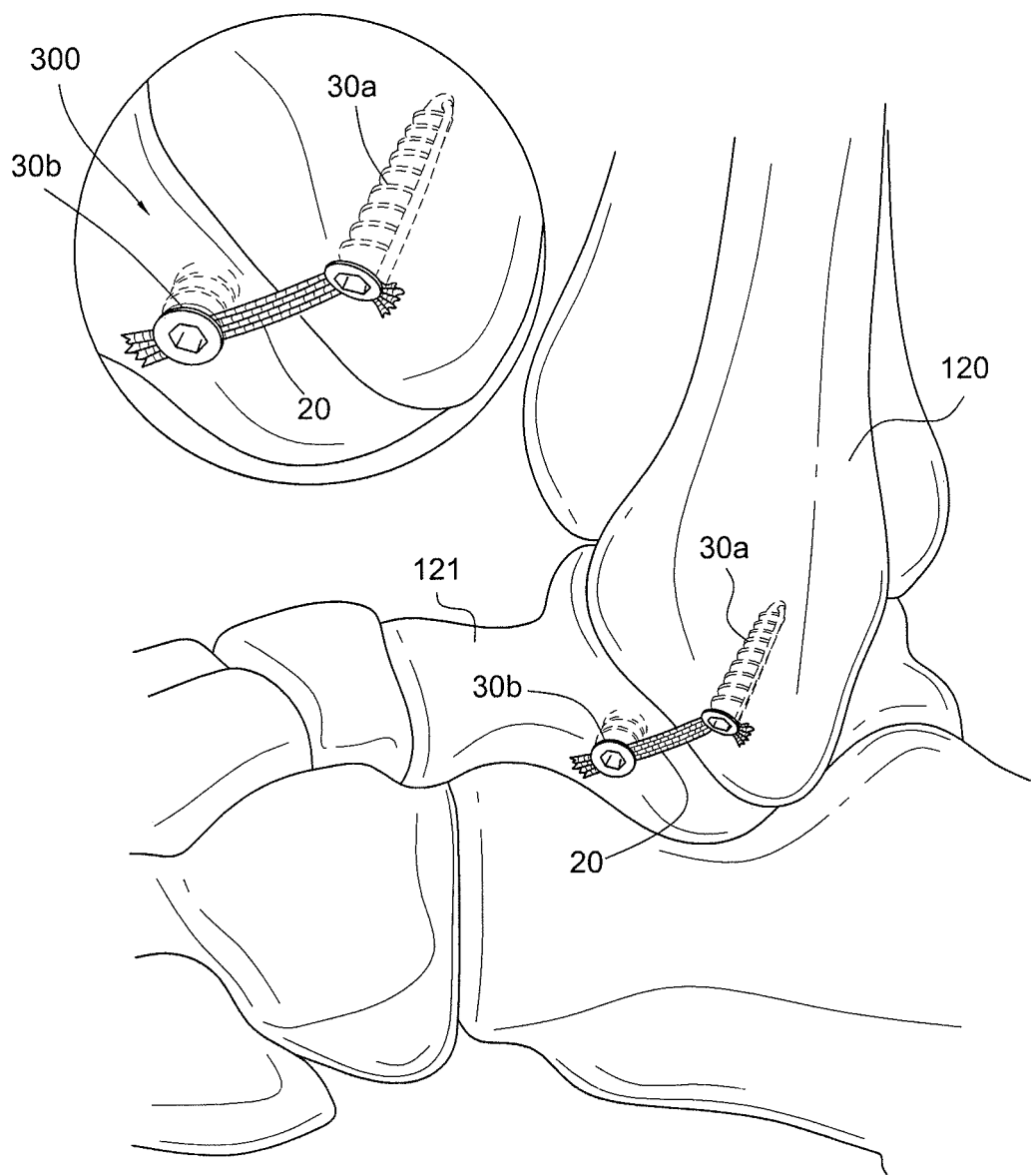
FIG. 13 illustrates another view of an ankle with ATFL reconstruction completed with an ATFL internal brace, and in accordance to the present invention.

The ATFL internal brace 300 is similar to the MCL internal brace 100 described above and comprises a replacement/reinforcement construct 20 (suture construct 20) attached to two fixation devices 30*a*, 30*b* (implants 30*a*, 30*b*), shown in more detail in FIG. 13. Suture construct 20 may be a suture tape such as FiberTape®, a combination of suture strand and suture tape, a collagen tape, or a suture with biological material. The suture construct may be also formed by cutting a patch into strips and using the strips with the fixation devices. Biological materials such as blood, blood , components, BMA, BMSCs, PRP, ACP and/or growth factors may be directly injected into the ligament injury site and small incisions, to further improve and accelerate incision and ligament healing, or may be provided via the suture construct (i.e., provided within the suture construct, for example).

The fixation devices 30*a*, 30*b* may include knotless fixation devices (such as push-in type anchors like the PushLock® C anchor, or anchors with a swivel tip like the SwiveLock® C anchor). The fixation devices 30*a*, 30*b* may be any anchors or screws (such as interference screws or tenodesis screws) or any combinations of anchors and screws. The fixation devices/implants 30*a*, 30*b* may have various sizes (various diameters and/or lengths) and may be formed of biocompatible materials such as PEEK, biocomposite materials, metals and/or metal alloys, or combination of such materials, among others.

The replacement/reinforcement construct 20 (suture construct 20) of ATFL 300 secured by the two inserted fixation devices 30*a*, 30*b* is about parallel to the anatomical orientation of the ATFL 150, i.e., extends along the longitudinal axis of the ATFL 150. Preferably, the length of the replacement/reinforcement construct 20 is about equal to the length of the anatomical ATFL 150 (FIG. 6) to be replaced and/or reinforced.

Figure 10:
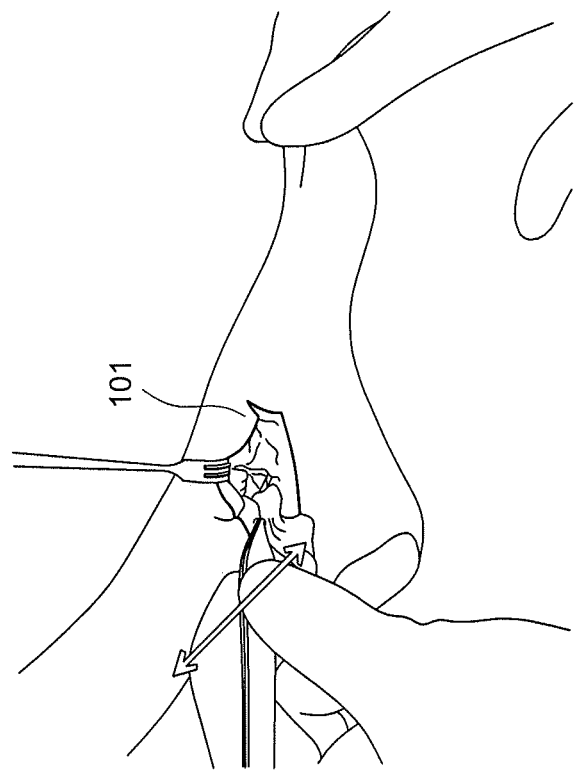
FIG. 10 illustrates an ATFL internal brace used in a method of ATFL reconstruction of the present invention (with plantar flexion (in line with tibia) and negative draw).
Figure 9:
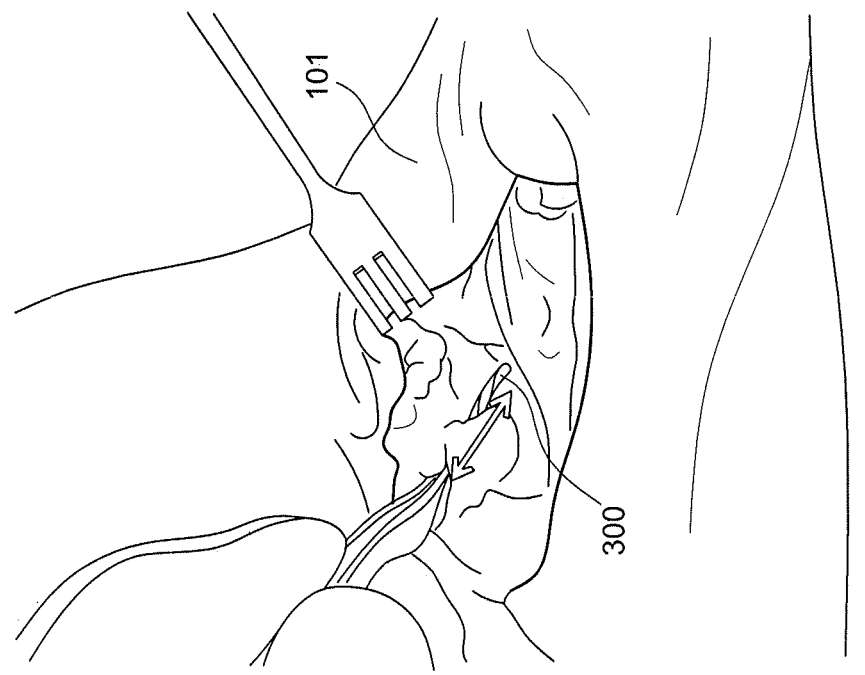
FIG. 9 illustrates an ATFL internal brace used in a method of ATFL reconstruction of the present invention (ATFL neutral).

FIG. 9 illustrates a dissection of the ankle of FIGS. 7 and 8, showing the ATFL internal brace 300 used in a method of ATFL reconstruction of the present invention (ATFL neutral). FIG. 10 illustrates the ATFL internal brace 300 with plantar flexion (in line with tibia) and negative draw.

Figure 11:
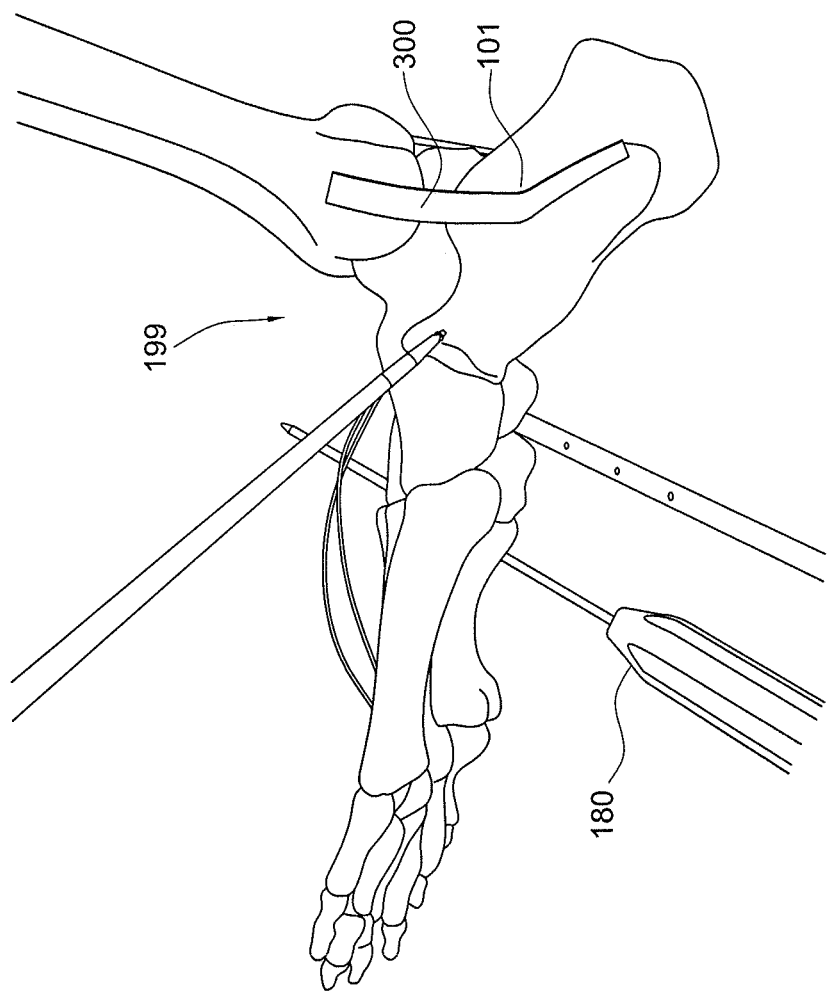
FIG. 11 illustrates a side view of an ankle undergoing ATFL reconstruction with an ATFL internal brace.
Figures 12A, 12B:
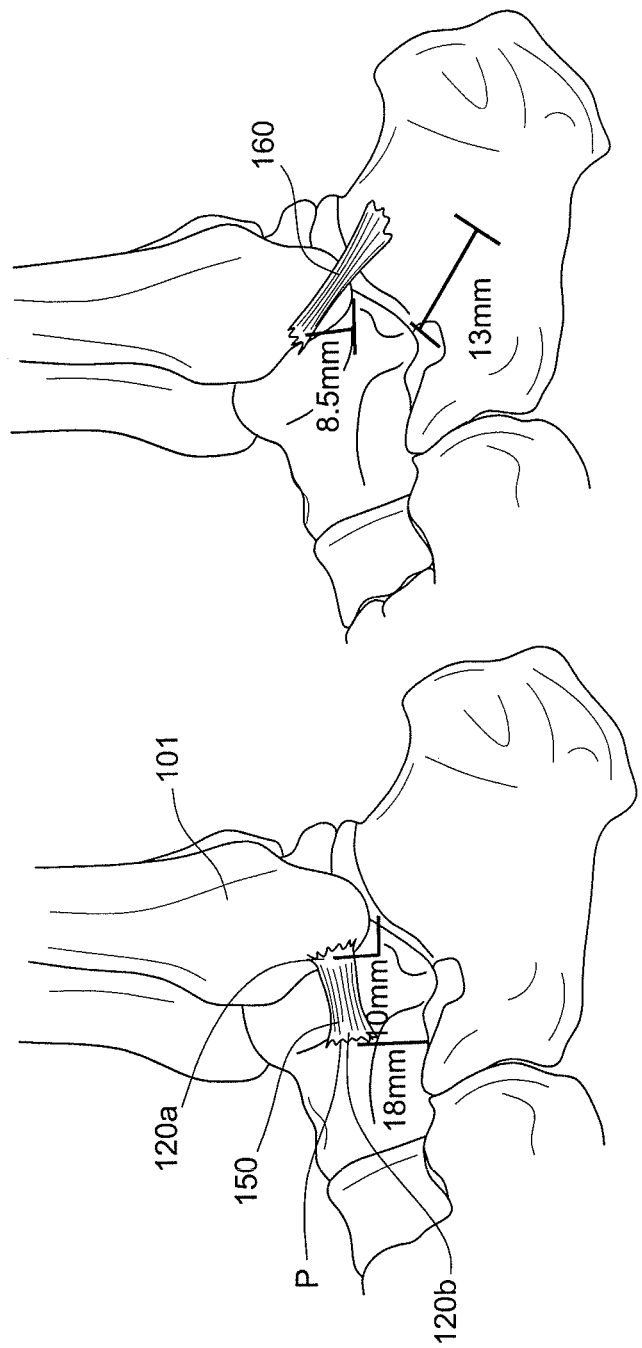
FIG. 12(a) illustrates a schematic, enlarged view of an ankle undergoing ATFL reconstruction (illustrating the insertion point of ATFL about 18 mm above the subtalar joint, just distal to the edge of the talar articular surface).
FIG. 12(b) illustrates a schematic, enlarged view of an ankle illustrating the insertion point of the calcaneofibular ligament.

FIG. 11 illustrates another side view of an ankle 101 undergoing ATFL reconstruction with ATFL internal brace 300 (with plantar flexion (in line with tibia) and negative draw) and with additional passing instrument(s) 180 as part of kit 199. FIG. 12(*a*) illustrates a schematic, enlarged view of portion of the ankle of FIG. 11 undergoing ATFL reconstruction (illustrating the insertion point "P" (120*b*) of ATFL 150 located about 18 mm above the subtalar joint, just distal to the edge of the talar articular surface). FIG. 12(*b*) illustrates a schematic, enlarged view of the ankle of FIG. 11 illustrating the insertion point of calcaneofibular ligament 160 (a collateral ligament of the ankle).

FIG. 13 illustrates an exemplary schematic view of a final repair/reinforcement with the ATFL internal brace 300, with braided suture tape construct 20 secured within fibula and talus by two knotless fixation devices 30*a*, 30*b* (for example, a 3.5 mm SwiveLock® anchor and a 4.75 mm SwiveLock® anchor).

Surgical steps for a method of ATFL reconstruction with ATFL internal brace 300 of the present invention are provided below (with reference to FIGS. 6-12):

The ankle 101 is placed in neutral position. Reference fibular insertion about 10 mm anterior and proximal to the tip of fibula 120. May use template and screen. The fixation devices 30*a*, 30*b* (for example, two SwiveLocks® anchor) are inserted in line of fibula 120 about 10 mm medial to the lateral cortex.

Design the basic template. Identify the insertion point of the ATFL 150 about 18 mm above the subtalar joint, just distal to the edge of the talar articular surface. Screen with template and pointer. Inset a fixation device (for example, screw or anchor 120*b*) about 18 mm superior to this point (FIG. 12).

Make about 1 cm longitudinal incision. Tunnel the blunt tipped curved suture passer 180 proximally between the two points. Retrieve the suture construct 20 (for example, a double strand FiberTape®).

Secure the suture construct 20 distally with SwiveLock® anchor 30b inserted about perpendicular to the cortex in neutral after testing range of motion (ROM) and stability.

Indications for ATFL InternalBrace (Accelerator) 300

Grade 2/3 lateral ligament injuries

More severe injuries may require CFL repair with second FiberTape® from same fibular attachment. The aim, however, is to accelerate rehabilitation and prevent attenuation of ligament complex during healing.

Surgical Benefits

Simple and safe

Time efficient procedure (about 30 min procedure)

Does not complicate a Brostrom procedure if subsequently required

Primary direct repair is not successful

Arthroscopic check at same time is optimal

ACP injections facilitate biological healing and recovery

Patient Benefits

Accelerated recovery

Optimal length for ligament healing

No need for cast

Internal brace may protect from future injury

Joint protection instability/arthritis

ACP injections to add to biological healing

The method of ATFL reconstruction/reinforcement detailed above offers a unique approach and a fundamental change to the management of acute ligament injuries such as the lateral ligament of ankle, medial ligament of knee and medial patellofemoral ligament, and acromioclavicular joint ligaments, among others. Together with biologics, the method acts as a primary intervention to improve outcomes. The procedure is minimally invasive.

Whether as suture repair alone, or with the addition of a tendon graft, the InternalBrace~ reconstruction system 300 can support the primary repair using two fixation devices 30a, 30b (for example, SwiveLock® anchors) in combination with FiberTape® 20, a uniquely blended form of UHMW polyethylene suture. In an exemplary embodiment only, the InternalBrace™ reconstruction system 300 consists of two SwiveLock® anchors 30a, 30b and a length of FiberTape® 20 (collagen coated material) between the two SwiveLock® anchors 30a, 30b.

Referring now to FIG. 13, another exemplary method of employing an internal brace 300 for ATF repair/reconstruction comprises the following steps: after predrilling the fibula 120 about 1 cm from the tip proximally, an initial 3.5 mm SwiveLock® 30a preloaded with FiberTape® 20 is placed axially in the fibular neck. After loading the talar anchor 30b (for example, a 4.75 mm SwiveLock® 30b) with the other end of the FiberTape® 20, a second hole is drilled at the site of the normal anatomic attachment of the ATF on the talus 121. The 4.75 mm anchor 30b is placed and the thumbpad is held steady until the anchor 30b is flush with the talus 121. A small hemostat can be placed under the FiberTape® 20 at the fibular/talar connection, thereby preventing over-tightening of the construct.

The internal brace 100, 200, 300 reconstruction system of the present invention may be provided as part of a ligament repair augmentation kit, to double the fixation strength of the ligament repair (for example, the lateral ankle ligament repair). This simple, safe and reproducible procedure augments the standard lateral ankle ligament repair procedure.

The InternalBrace™ reconstruction system offers the surgeon and patient many benefits. After the procedure, no cast is needed and early mobilization can start which will improve patient comfort. The potential for earlier recovery exits as the FiberTape® bridge between the fibula and talus parallels the ATF ligament, adding much needed support for the ligaments to heal in the normal anatomic position. The implant kit construct, which includes exemplary 3.5 mm and 4.75 mm SwiveLock® anchors, anchors the construct with the robust FiberTape® bridge. The strength of this construct may allow the surgeon the option of leaving the peroneal brevis tendon intact, assuming the surgeon would use a portion of this for another augmentation procedure. This construct may also offer resistance against future injury, providing some joint protection against instability and associated arthritis.

The procedure is simple, safe and reproducible. The procedure augments the stability provided by the standard lateral ankle ligament repair for either an acute or chronic pathology. The procedure doubles the repair strength over the Brostrom procedure. The construct may allow some surgeons the option of leaving the peroneal brevis tendon intact, if normally used for augmentation of the standard repair.

The procedure may be a knotless repair, utilizing two SwiveLock® anchors (3.5 mm for fibula/4.5 mm for talus) and FiberTape® (for example, a collagen coated material). The FiberTape® can be cut flush to offer a true knotless repair.

For post op recovery, the FiberTape® bridge parallels the ATF ligament, adding much needed support for the ligaments to heal in the normal anatomic position. This offers the potential for early mobilization, which in turn can improve patient comfort. The construct may offer added resistance against future injury, while providing some joint protection against instability and arthritis.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed as new and desired to be protected by Letters Patent of the United States is:

1. A method of surgical repair, comprising:
   inserting a first fixation device into a femur at a first location that is adjacent to a femoral attachment point of a medial collateral ligament (MCL);
   establishing a tunnel that extends from the first location to a second location that is adjacent to a tibial attachment point of the MCL;
   shuttling a suture construct that is connected to the first fixation device from the first location to the second location,
   wherein shuttling the suture construct includes passing the suture construct between the MCL and skin, muscle, and fascia overlying the MCL;
   connecting the suture construct to a second fixation device; and
   inserting the second fixation device into a tibia at the second location,
   wherein, after inserting the first and second fixation devices, the suture construct extends over the MCL to reinforce the MCL.

* * * * *